US012622700B2

(12) United States Patent
O'Halloran et al.

(10) Patent No.: US 12,622,700 B2
(45) Date of Patent: May 12, 2026

(54) SYSTEM COMPRISING AN ELONGATED CATHETER AND AN IMPLANT DETACHABLY ATTACHED TO A DISTAL END OF THE ELONGATED CATHETER

(71) Applicant: AURIGEN MEDICAL LIMITED, Galway (IE)

(72) Inventors: Tony O'Halloran, Turloughmore County Galway (IE); John Thompson, Dublin (IE); Shane Regan, Loughrea County Galway (IE); Kevin Donaghey, An Spideal County Galway (IE); John Kelly, Salthill County Galway (IE); Conor Allen, Cappagh Road County Galway (IE)

(73) Assignee: AURIGEN MEDICAL LIMITED, Galway (IE)

( * ) Notice: Subject to any disclaimer, the term of this patent is extended or adjusted under 35 U.S.C. 154(b) by 973 days.

(21) Appl. No.: 17/863,235

(22) Filed: Jul. 12, 2022

(65) Prior Publication Data
US 2023/0012824 A1 Jan. 19, 2023

(30) Foreign Application Priority Data
Jul. 13, 2021 (EP) ..................................... 21185453

(51) Int. Cl.
*A61B 17/12* (2006.01)
*A61B 18/14* (2006.01)
*A61B 17/00* (2006.01)

(52) U.S. Cl.
CPC .... *A61B 17/12022* (2013.01); *A61B 18/1492* (2013.01); *A61B 2017/00575* (2013.01)

(58) Field of Classification Search
CPC ........ A61B 17/12022; A61B 17/12122; A61B 17/12172; A61B 17/12177;
(Continued)

(56) References Cited

U.S. PATENT DOCUMENTS 4,909,789 A 3/1990 Taguchi et al.
5,573,530 A 11/1996 Fleury et al.
(Continued)

FOREIGN PATENT DOCUMENTS

EP 3399933 B1 11/2018
WO 0187168 A1 11/2001
(Continued)

OTHER PUBLICATIONS

EPO Search Report issued in European Patent Application No. 21185453.4, dated Jan. 18, 2022.

*Primary Examiner* — Ankit D Tejani
*Assistant Examiner* — Joshua Brendon Solomon
(74) *Attorney, Agent, or Firm* — Bookoff McAndrews, PLLC

(57) ABSTRACT

A system includes an elongated catheter including a proximal end configured for operative coupling to an electrical power source, a distal end with a first electrical connector and a first conducting wire, an implant including a tissue energising module and a proximal connecting hub configured to detachably couple with the distal end of the elongated catheter. The proximal connecting hub includes a second electrical connector configured to mate with the first electrical connector and electrically couple the first electrical connector with the tissue energising module through a second conducting wire. A latch system to lock the distal end of the catheter to the proximal connecting hub arm includes an arm attached to the distal end of the catheter that is resiliently deformable such that the arm engages a sidewall of the proximal connecting hub and a locking element that is axially adjustable.

15 Claims, 6 Drawing Sheets

(58) Field of Classification Search
  CPC ...... A61B 18/1492; A61B 2017/00575; A61B
                 2017/00026; A61B 2017/12054; A61B
                 2017/00243; A61B 2018/00172; A61B
                 2018/00357; A61B 2018/00178; A61B
                           2018/00577; A61B 2018/1467
  See application file for complete search history.

(56)                    References Cited

U.S. PATENT DOCUMENTS

| | | | |
|---|---|---|---|
| 6,454,775 | B1 | 9/2002 | Demarais et al. |
| 6,652,548 | B2 | 11/2003 | Evans et al. |
| 2004/0219028 | A1 | 11/2004 | Demarais et al. |
| 2009/0306655 | A1* | 12/2009 | Stangenes ......... A61M 25/0069 |
| | | | 606/41 |
| 2020/0046423 | A1 | 2/2020 | Viswanathan et al. |
| 2020/0121324 | A1 | 4/2020 | O'Halloran et al. |
| 2020/0139114 | A1 | 5/2020 | Viswanathan et al. |
| 2020/0230403 | A1 | 7/2020 | Bowers et al. |
| 2020/0253615 | A1 | 8/2020 | Melanson et al. |
| 2020/0383668 | A1 | 12/2020 | Rafiee et al. |

FOREIGN PATENT DOCUMENTS

| | | | |
|---|---|---|---|
| WO | 2013109756 | A2 | 7/2013 |
| WO | 2018185255 | A1 | 10/2018 |
| WO | 2018185256 | A1 | 10/2018 |
| WO | 2019157359 | A1 | 8/2019 |
| WO | 2020074738 | A1 | 4/2020 |

* cited by examiner

SYSTEM COMPRISING AN ELONGATED CATHETER AND AN IMPLANT DETACHABLY ATTACHED TO A DISTAL END OF THE ELONGATED CATHETER

CROSS REFERENCE TO RELATED APPLICATION

This application claims priority from European Patent Application 21185453.4, filed on Jul. 13, 2021, the entire contents of which being incorporated herein by reference.

FIELD OF THE INVENTION

The present invention relates to a system comprising an elongated catheter and an implant detachably attached to a distal end of the elongated catheter.

BACKGROUND TO THE INVENTION

Catheter systems comprising elongated catheters and an implant detachably attached to a distal end of the elongated catheter are described in the literature—see for example WO2018185256, WO2018185255 and WO2020074738 in which the implant is an occlusion device for occluding a body lumen such as the left atrial appendage, and in which the catheter is employed to deliver the implant percutaneously to a target site, the implant is deployed and then released from the catheter. The implants often include electrically active modules, for example tissue ablation electrodes or sensors, that require an electrical supply, and in most cases the catheter is configured for electrically coupling the electrode or sensor with an external power supply. This requires that the distal end of the catheter can mechanically connect to the implant in a secure manner, and also electrically connect to the implant. As the implant is used in the vasculature which is a wet environment, the electrical connection is best provided in the form of pins at the end of the catheter (or implant) and corresponding sockets for receiving the pins on the implant (or catheter) that electrically couple and decouple by axial movement of the catheter relative to the implant. This means that the use of threaded engagement between the catheter and implant is not practical, as when the pins are engaged in corresponding sockets, relative rotational movement between the catheter and implant is not possible.

It is an objective of the invention to overcome at least one of the above-referenced problems.

SUMMARY OF THE INVENTION

The objective is met by the provision of a catheter with a distal end comprising a first electrical connector (with e.g. one of pins or sockets), and an implant with a proximal connecting hub comprising a second electrical connector (with e.g. another of pins or sockets), in which the connectors are configured to electrically couple and decouple by axial movement of the catheter relative to the implant. In addition, the end of the catheter comprises one or more latching arms that in an un-tensioned configuration extend distally and radially outwardly (See FIG. 1) and are resiliently deformable into a tensioned latched configuration in which the arms engage the hub (See FIG. 4). A locking element is provided that is adjustable to lock the arm in the latched configuration. In one embodiment, the locking element is a bolt or element that is axially movable from an extended configuration in which an end of the bolt/element engages the arm in the latched configuration (See FIG. 5) and a retracted configuration in which the end of the bolt/element does not engage the arm allowing the arm return to the unlatched and un-tensioned configuration (See FIG. 3). The arm generally includes a terminal grab section with a bolt receiving socket, and the hub comprises an aperture configured to receive the grab section such that the bolt engages the socket of the grab section generally inside the hub. The system allows the device to be assembled outside the body with the catheter mechanically coupled and electrically connected to the hub of the implant, and the device is then used to treat or sense parameters of tissue, for example to ablate tissue in a body lumen. During these stages, the arm is locked in the tensioned latched configuration by the locking bolt(s) which is/are extended. Once the treatment is completed, the locking bolts can be retracted (generally using a controller on a handle of the catheter) which allows the arms return to the un-tensioned outwardly biased shape, and the catheter is then released from the implant and can be retracted to leave the implant in situ. Although the embodiments described herein show the latching arm having a radially outward un-tensioned configuration, it will be appreciated that the same technical effect can be achieved with a latching arm having a radially inward un-tensioned configuration that is adjustable to a tensioned configuration in which the arm engages an inside of the hub. In this embodiment, during assembly, the radially inward arm or arms can be forced into engagement with the inside of the hub sidewall by inserting an expander into the hub to force the arms into engagement with the inside of the hub as illustrated in FIGS. 6A-6C. FIGS. 7-9 illustrate a deployed implant with a proximal connecting hub disposed in a recess in a proximal end of the implant.

In a first aspect, there is provided a system comprising:

an elongated catheter comprising a proximal end configured for operative coupling to an electrical power source, a distal end with a first electrical connector and a first conducting wire to electrically couple the electrical power source with the first electrical connector;

an implant comprising a tissue energising module and a proximal connecting hub configured to detachably couple with the distal end of the elongated catheter by axial movement of the elongated catheter relative to the proximal connecting hub, the proximal connecting hub comprising a second electrical connector configured to mate with the first electrical connector and electrically coupled the first electrical connector with the tissue energising module through a second conducting wire; and a latch system to lock the distal end of the catheter to the proximal connecting hub.

The latch system generally comprises:

an arm attached to the distal end of the catheter that extends distally and is resiliently deformable from an untensioned un-latched configuration to a tensioned latched configuration in which the arm engages the sidewall of the proximal connecting hub; and a locking element that is adjustable to lock the arm in the latched configuration.

In any embodiment, the locking element is a locking bolt disposed in the distal end of the catheter that is axially adjustable from a retracted position to a distally extended position in which the bolt engages the arm in the latched configuration.

In any embodiment, the or each arm extends radially outwardly or radially inwardly (e.g. is curved inwardly or outwardly) in a relaxed configuration and is resiliently deformable into the tensioned latched configuration.

In any embodiment, the or each arm is substantially straight when in the tensioned latched configuration.

In any embodiment, the arm is configured to engage an aperture in the sidewall of the proximal connecting hub when in the tensioned latched configuration.

In any embodiment, the proximal connecting hub comprises a sidewall with an aperture, and the arm comprises a grab part with a socket configured to protrude through the aperture when the arm is in the tensioned latched configuration, wherein the locking bolt is configured to engage the socket when in the distally extended orientation.

In any embodiment, the system comprises a first latch comprising a first arm and a first locking bolt disposed on one side of the distal end of the catheter and a second latch comprising a second arm and a second locking bolt disposed on an opposite side of the distal end of the catheter.

In any embodiment, the sidewall of the proximal connecting hub comprises a recess to receive the or each arm whereby when the arm is in the latched configuration, the arm is flush with a surface of the sidewall.

In any embodiment, the distal end of the catheter comprises a distal face and the proximal end of the proximal connecting hub comprises a proximal face, wherein distal and proximal faces abut when the catheter and proximal connecting hub are coupled together, and wherein the distal face comprises the first electrical connector and the proximal face comprises the second electrical connector.

In any embodiment, the first electrical connector comprises a first section disposed on one side of the distal face and a second section disposed on an opposite side of the distal face and the second electrical connector comprises an first section disposed on one side of the distal face and a second section disposed on an opposite side of the distal face.

In any embodiment, the or each tissue energising module comprises a tissue ablation electrode.

In any embodiment, the implant is a radially expansible occlusion apparatus for occluding a body lumen and is adjustable between a contracted orientation suitable for transluminal delivery and a deployed orientation configured to occlude the body lumen.

In any embodiment, the implant is a radially expansible occlusion apparatus for occluding a left atrial appendage of the heart.

In any embodiment, the proximal connecting hub of the implant comprises an annular sidewall that defines an open proximal end and two wing elements mounted to the sidewall on opposed sides of the open proximal end that are configured for movement from an at rest closed configuration in which the wing elements are folded over the open proximal end of the raised connecting hub to an open tensioned configuration.

In any embodiment, a radially outer wall of the distal end of the catheter comprises surface recesses configured to receive the wing elements of the proximal connecting hub in a nested flush configuration when the distal end of the catheter and proximal connecting hub are connected together.

In any embodiment, the one of the first electrical connector and second electrical connector comprises a housing with one or more electrical sockets and another of the first electrical connector and second electrical connector comprises a housing with one or more electrical pins corresponding to the one or more electrical sockets. Provision of a pin and socket electrical connection electrically insulates the connector to prevent the system shorting when in a liquid environment such as the vasculature.

In any embodiment, the housing of the electrical connector comprising the or each electrical pin comprises a resiliently deformable sidewall in which the or each electrical pin projects proud of the resiliently deformable sidewall.

In any embodiment, the elongated catheter comprises a plurality of first conducting wires electrically connected to the first electrical connector, and the tissue energising module comprises a plurality of electrodes each connected to the second electrical connector by a dedicated second conducting wire, wherein the first and second electrical connectors are configured to mate to electrically couple each first conducting wire with a corresponding second conducting wire. In this manner, the implant may have a plurality of tissue ablation electrodes, each of which has its own power supply allowing the electrodes to be actuated independently. For example, the elongated catheter may comprise at least four, six, eight or ten first conducting wires electrically connected to the first electrical connector, and the tissue energising module may comprise corresponding electrodes each connected to the second electrical connector by a dedicated second conducting wire.

In any embodiment, the tissue energising module comprises tissue ablation electrodes. In any embodiment, the tissue energising module comprises sensing electrodes.

In any embodiment, the implant is an implantable occlusion apparatus (typically radially expansible) for occluding a body lumen and is adjustable between a contracted orientation suitable for transluminal delivery and a deployed orientation configured to occlude the body lumen.

In any embodiment, the implant is a radially expansible occlusion apparatus for occluding a left atrial appendage of the heart.

In any embodiment, the radially expansible occlusion apparatus comprises:

a cylindrical cage body having a sidewall, an optionally open distal end and a concave proximal end wall and a raised proximal connecting hub with an open proximal end typically providing a through lumen into the cylindrical cage body; and a cover proximal of the raised connecting hub having a closable aperture providing access to the raised connecting hub from a proximal side of the occlusion apparatus.

In any embodiment, the proximal connecting hub of the implant comprises an open proximal end defined by an annular sidewall and two wing elements mounted on opposed sides of the annular sidewall that are configured for movement from an at rest closed configuration in which the wing elements are folded over the open proximal end of the raised connecting hub to an open tensioned configuration in which the wing elements extend proximally annular sidewall.

In any embodiment, the wings are typically connected to the cover on each side of the aperture whereby when the wings are in the closed configuration the aperture in the cover is closed to prevent movement of blood through the raised connecting hub.

In any embodiment, the wings are formed from a shape memory material and are biased into the closed configuration.

In any embodiment, the cover comprises a first cover part attached to one wing and a second part attached to a second wing.

In any embodiment, the first and second cover parts are semi-circular.

In any embodiment, the two parts are configured to at least partially overlap when the wings are in the closed configuration.

In any embodiment, one of the first electrical connector and second electrical connector comprises a housing with one or more electrical sockets (female connector) and another of the first electrical connector and second electrical connector comprises a housing with one or more electrical pins (male connector) corresponding to the one or more electrical sockets.

In any embodiment, the second electrical connector comprises a housing with one or more electrical sockets and the first electrical connector comprises a housing with one or more electrical pins corresponding to the one or more electrical sockets.

In any embodiment, the male electrical connector comprises a resiliently deformable sidewall part in which the or each electrical pin projects proud of the resiliently deformable sidewall part. The provision of a resiliently deformable sidewall part around the pins allows the electrical connectors tightly abut and fluidically isolate the pins and sockets.

In any embodiment, the system comprises an electrical controller coupled to an electrical power source and the or each conducting wire of the catheter and configured to energise the or each tissue energising module of the implant when the implant and catheter are electrically coupled.

In another aspect, there is provided a method comprising the steps of providing a system according to the disclosure with the proximal hub of the implant connected to the distal end of the catheter and first electrical connector electrically coupled to the second electrical connector and in which the or each arm is locked by the locking element in a tensioned latched configuration;

advancing the catheter and implant transluminally to a target site in a body lumen;

electrically energising the or each tissue energising module of the implant;

decoupling the implant from the distal end of the catheter by moving the or each locking element into the retracted position to allow the or each arm return to a unlatched configuration; and withdrawing the elongated catheter transluminally to leave the implant in-situ.

In any embodiment, the method is a method of ablating tissue of the body lumen, for example tissue of a left atrial appendage.

In any embodiment, the or each arm is untensioned when it is in an unlatched configuration.

In any embodiment, the arm is locked by the locking element in a radially inward or radially outward configuration.

In any embodiment, the locking element is locking arm. The locking arm is generally configured for axial movement to lock or unlock the or each arm.

Other aspects and preferred embodiments of the invention are defined and described in the other claims set out below.

DETAILED DESCRIPTION

Figure 1:
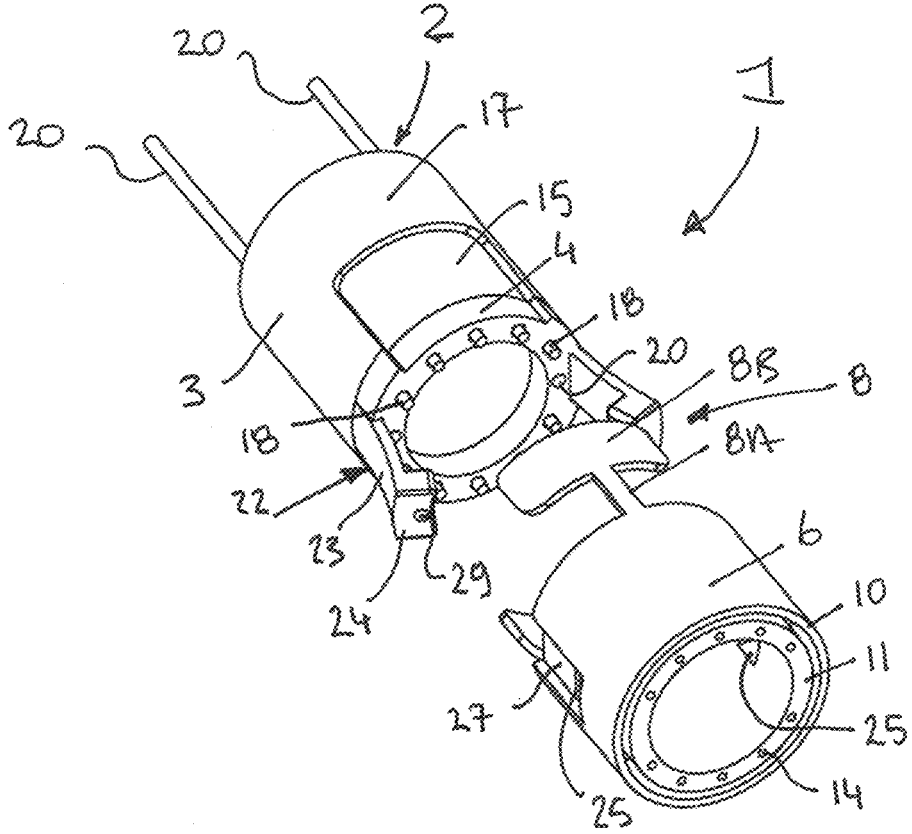
FIG. 1 is a perspective view of a catheter and proximal connecting hub forming part of the system of the invention in a decoupled configuration with the latching arms in an un-tensioned radially outward unlatched configuration.

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the a etiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of a PFA treatment to a subject) which cures, ameliorates or lessens the symptoms of a disease or removes (or lessens the impact of) its cause(s). In this case, the term is used synonymously with the term "therapy".

Additionally, the terms "treatment" or "treating" refers to an intervention (e.g. the administration of a PFA treatment to a subject) which prevents or delays the onset or progression of a disease or reduces (or eradicates) its incidence within a treated population. In this case, the term treatment is used synonymously with the term "prophylaxis".

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, assess, kiang and zebra.

"Implantable occlusion apparatus" means an apparatus configured for implantation in a body lumen, especially implantation in the heart at least partially or fully within the left atrial appendage, and upon actuation to at least partially or fully fluidically occlude the body lumen. The occlusion apparatus is typically detachably connected to a delivery catheter which delivers the occlusion apparatus to the target site, and typically remains attached during occlusion, sensing and energy delivery treatments and in one embodiment is generally detached after the energy delivery treatment and removed from the body leaving the occlusion apparatus implanted in the body lumen. Occlusion may be complete occlusion (closing) of the body lumen or partial occlusion (narrowing of the body lumen or near complete occlusion). The occlusion apparatus typically comprises a body that is radially expansible from a contracted delivery configuration to an expanded deployed configuration (radially expansible occlusion apparatus). The body may take many forms, for example a wireframe structure formed from a braided or meshed material. Examples of expandable wireframe structures suitable for transluminal delivery are known in the literature and described in, for example, WO01/87168, U.S. Pat. No. 6,652,548, US2004/219028, U.S. Pat. Nos. 6,454, 775, 4,909,789, 5,573,530, WO2013/109756. Other forms of bodies suitable for use with the present invention include plate or saucer shaped scaffolds, or stents. In one embodiment, the body is formed from a metal, for example a shape-memory metal such as nitinol. The body may have any shape suitable for the purpose of the invention, for example cylindrical, discoid or spheroid. In one preferred embodiment, the apparatus comprises a cylindrical body, for example a cylindrical cage body. In one embodiment, the body comprises a tissue energising module. In one embodiment, the ablation device comprises an array of electrodes, typically a circumferential array. In one embodiment, the array of electrodes are configured to deliver pulsed field ablation to the tissue. In one embodiment, a distal face of the radially expansible body comprises a covering configured to promote epithelial cell proliferation. In one embodiment, the body comprises a stepped radial force stiffness profile from distal to proximal device. In one embodiment, the body comprises a metal mesh cage scaffold. In one embodiment, a coupling between the body and the catheter member is located distally to the left atrial facing side of the body. In one embodiment, the body in a deployed configuration has a radial diameter at least 10% greater than the radial diameter of the left atrial appendage at a point of deployment. In one embodiment, the furthermost distal part is configured to be atraumatic to cardiac tissue. In one embodiment, the body comprises a braided mesh scaffold that in one embodiment is conducive to collagen infiltration on thermal energy delivery to promote increased anti migration resistance. Examples of an implantable occlusion apparatus for use in a body lumen especially the LAA are described in WO2018/185256, WO2018/185255 and WO2020/074738.

"Body lumen" means a cavity in the body, and may be an elongated cavity such as a vessel (e.g. an artery, vein, lymph vessel, urethra, ureter, sinus, auditory canal, nasal cavity, bronchus) or an annular space in the heart such as the left atrial appendage, left ventricular outflow tract, the aortic valve, the mitral valve, mitral valve continuity, or heart valve or valve opening.

"Detachably attached" or "detachably coupled" means that the device is configured such that the occlusion apparatus is attached to the elongated delivery catheter during delivery and can be released after deployment and treatment whereby the occlusion apparatus is implanted in the heart and the elongated delivery catheter can be withdrawn leaving the occlusion apparatus in-situ. Typically, the device includes a control mechanism for remotely detaching the occlusion apparatus or radially expansible element from the elongated catheter member. Typically, an actuation switch for the control mechanism is disposed on the control handle.

"Transluminal delivery" means delivery of the occlusion apparatus to a target site (for example the heart) heart through a body lumen, for example delivery through an artery or vein. In one embodiment, the device of the invention is advanced through an artery or vein to deliver the occlusion apparatus to the left atrium of the heart and at least partially in the LAA. In one embodiment, the device is delivered such that the distal part is disposed within the LAA and the proximal part is disposed in the left atrium just outside the LAA. In one embodiment, the device is delivered such that the distal part is disposed within the LAA and the proximal part is disposed in the left atrium abutting a mouth of the LAA. In one embodiment, the device is delivered such that both the distal and proximal parts are disposed within the LAA.

"Cover": Typically, the implantable occlusion apparatus has a proximal cover which is impermeable to blood and that may include a re-closable aperture, for example an overlapping flap of material. The re-closable aperture may be configured to allow a distal end of the catheter through the aperture while preventing blood flow through the aperture. The occlusion apparatus may include a connecting hub distal of the cover and configured for coupling with a distal end of the catheter. The cover may be configured to act as a scaffold for in-vivo endothelialization. The cover may be formed from a woven mesh material.

"Covering/cover configured to act as a scaffold for in-vivo endothelialization" means a material that is use promotes epithelialization of the distal or proximal body. In one embodiment, the covering is a membrane that comprises agents that promote epithelial cell proliferation. Examples include growth factors such as fibroblast growth factor, transforming growth factor, epidermal growth factor and platelet derived growth factor, cells such as endothelial cells or endothelial progenitor cells, and biological material such as tissue or tissue components. Examples of tissue components include endothelial tissue, extracellular matrix, submucosa, dura mater, pericardium, endocardium, serosa, peritoneum, and basement membrane tissue. In one embodiment, the covering is porous. In one embodiment, the covering is a biocompatible scaffold formed from biological material. In one embodiment, the covering is a porous scaffold formed from a biological material such as collagen. In one embodiment, the covering is a lyophilised scaffold.

"Tissue energising module" as used herein refers to one or more electrodes disposed on the implantable occlusion apparatus configured for electrical coupling with an energy supply module via the catheter and electrical connectors. The electrodes are generally individually coupled with the energy supply module to allow electrode specific energising. They array of electrodes is generally arranged on the implantable occlusion apparatus in a circumferential arrangement and configured to contact the wall of the body lumen in a circumferential pattern when the apparatus is deployed. The electrodes are configured to deliver energy, generally PFA, circumferentially around the wall of the body lumen. The electrodes may also function as sensors to detect an electrical parameter of the tissue of the wall of the body lumen, for example electrical impedance or electrical activity (voltage). The electrodes may be configured to measure an electrical parameter radially across the wall of the body lumen, or circumferentially along a section of the circumference of the wall of the body lumen. Generally, measuring an electrical parameter such as electrical impedance radially across the wall of the body lumen employs an electrode of the array of electrodes and an earth or ground pad placed on the patient's body, often the leg. Measuring an electrical parameter such as electrical impedance circumferentially along a section of the body lumen employs two electrodes where one electrode functions as an energising electrode and the other functions as a detecting electrode. The electrical parameter such as electrical impedance may be measured at one frequency or over a range of frequencies.

The system of the invention may include an electrical controller. "Electrical controller" refers to a energy delivery generator, generally a pulsed field energy delivery generator, that comprises or can be operably coupled to an electrical power source and is operatively coupled to the tissue energising module of the implant (e.g. a plurality of electrodes) and configured to energise the electrodes, typically in a pulsed field ablation modality. In one preferred aspect, the controller comprises a signal generator configured for generating a pulse waveform. In any embodiment, the signal generator is configured to deliver at least one train of PFA energy to an electrode. In any embodiment, the signal generator is configured to deliver a train of energy of at least 20 pulses to an electrode. In any embodiment, the signal generator is configured to deliver at least one train of energy comprising an inter-phase delay of between 0 μs and 100 μs. In any embodiment, the signal generator is configured to deliver a train of energy comprising an inter-pulse delay of 1 to 100 μs, and typically at least 5 μs. In any embodiment, the signal generator is configured to deliver a train of energy comprising a pulse width of 100 ns-100 μs. In any embodiment, the signal generator is configured to deliver at least one train of PFA energy having a voltage amplitude between 100V and 5000V. In any embodiment, the signal generator is configured to deliver pulses in monophasic or biphasic form. The electrical controller is operably coupled to some or all of the electrodes (or electrode pairs) in the array in a manner allowing electrode pairs to be energised independently. The electrical controller may a comprise a plurality of electrode channels, and optionally a routing channel. Such an electrical controller is described in US2020230403. Electrical controllers for generating pulsed field ablative energy are described in EP3399933, US2020046423, WO2019157359 and US2020139114. Fraczek et al. describes the use of two electrodes or four electrodes to measure electrical impedance in tissue.

The system of the invention may be employed to treat atrial fibrillation typically by treating the left atrial appendage (LAA) to ablate LAA tissue or electrically occlude the LAA. "Atrial fibrillation" or "AF" is a common cardiac rhythm disorder affecting an estimated 6 million patients in the United States alone. AF is the second leading cause of stroke in the United States and may account for nearly one-third of strokes in the elderly. In greater than 90% of cases where a blood clot (thrombus) is found in the AF patient, the clot develops in the left atrial appendage (LAA) of the heart. The irregular heartbeat in AF causes blood to pool in the left atrial appendage, because clotting occurs when blood is stagnant, clots or thrombi may form in the LAA. These blood clots may dislodge from the left atrial appendage and may enter the cranial circulation causing a stroke, the coronary circulation causing a myocardial infarction, the peripheral circulation causing limb ischemia, as well as other vascular beds. The term includes all forms of atrial fibrillation, including paroxysmal (intermittent) AF and persistent and longstanding persistent AF (PLPAF).

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 4:
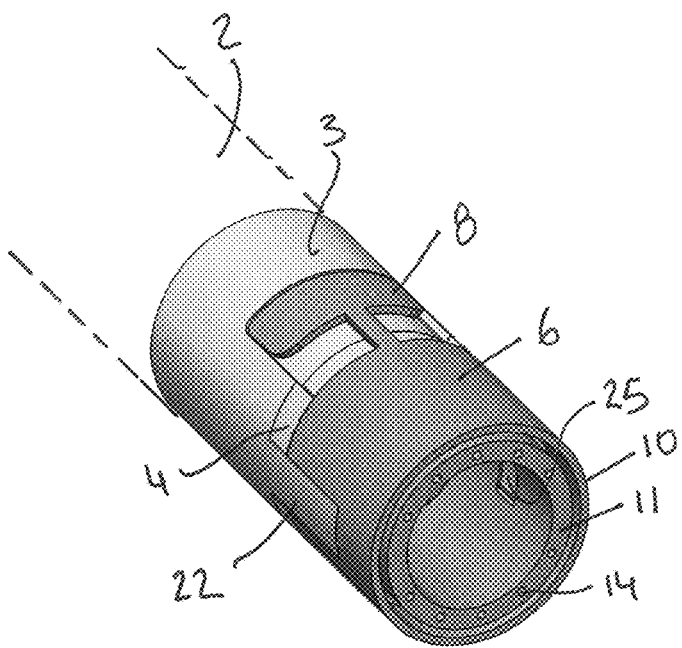
FIG. 4 is a perspective view of a catheter and proximal connecting hub of FIG. 1 in a decoupled configuration with the latching arms in an axial tensioned latched configuration.
Figure 5:
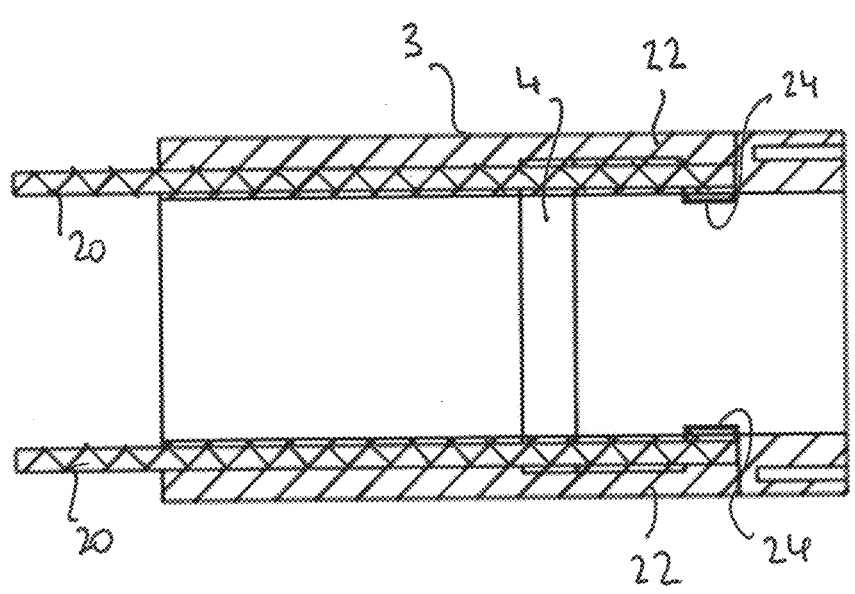
FIG. 5 is a sectional view of the catheter and proximal connecting hub of FIG. 4 (coupled configuration) showing the locking bolt in an extended configuration engaging the socket in the grab part of the latching arm inside the connecting hub.
Figures 7, 8, 9:
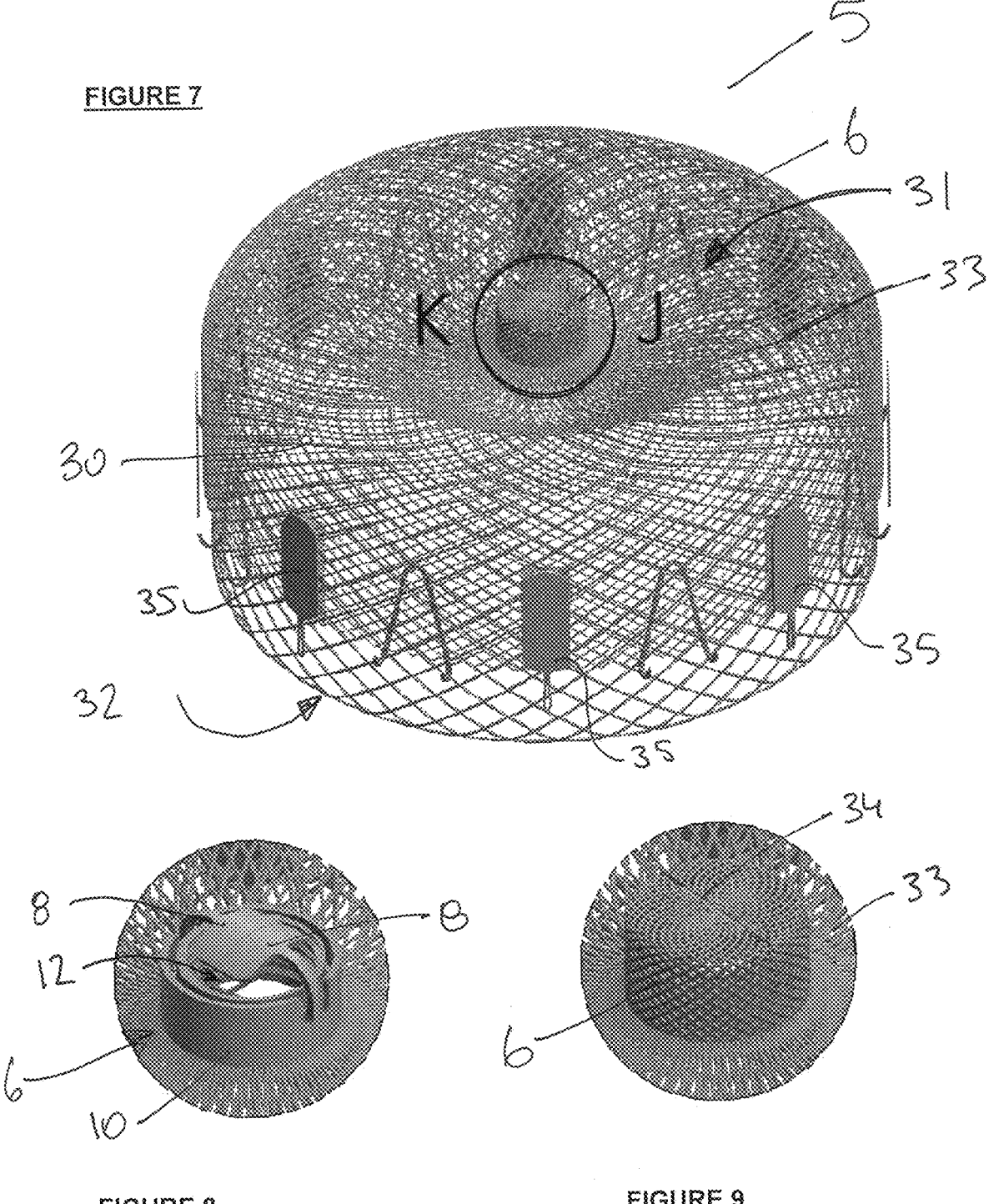
FIG. 7 is a perspective view of an implantable occlusion apparatus forming part of the system of the invention showing the concave proximal end and proximal connection hub.
FIG. 8 is a detailed view of the proximal connecting hub with the cover layer removed to showing the open proximal end and two wing elements mounted on opposed sides of the open proximal end in a closed configuration.
FIG. 9 is a detailed view of the proximal connecting hub with the cover layer shown covering the open proximal end.

Referring to the drawings, there is illustrated a system according to the invention indicated generally by the reference numeral 1 and comprising an elongated catheter 2 (only a distal part is shown) having a distal end 3 and first electrical connector 4, and a proximal connection hub 6 of an implant. FIGS. 1 to 5 only show the proximal connecting hub of the implant, and the full implant is illustrated in FIGS. 7 and 9 and is described in more detail below. In this example, the implant is a radially expansible occlusion apparatus for occlusion of the left atrial appendage (LAA) of the heart that is adjustable between a contracted orientation suitable for transluminal delivery (not shown) and a deployed orientation configured to occlude the LAA (shown). In FIGS. 4 and 5, the system is shown with the hub 6 (of the implant 5) attached to the catheter 2. This is how the device is assembled prior to use, and the configuration used to deliver the implant to the LAA. During transluminal delivery the occlusion apparatus is contracted and only deployed once the occlusion apparatus is positioned correctly (which can be confirmed using contrast dye or X-ray imaging). Once in position, the occlusion apparatus is deployed into circumferential contact with the wall of the LAA and the electrodes of the occlusion apparatus may then be energised to perform a tissue ablation treatment or to sense a parameter such as electrical impedance of the tissue. During a treatment or sensing procedure, the electrodes 9 are energised by electrical power supplied by an external energy supply via conducting wires in the catheter and occlusion apparatus.

Referring to FIGS. 1 to 5, the proximal connecting hub has an open end 12 defined by an outer annular sidewall 10 and a second electrical connector in the form of an inner annular sidewall 11. The inner annular sidewall comprises ten electrical sockets (not shown) and electrically conducting wires 14 that extend distally through the annular sidewall and into the implant (as described in more detail below with reference to FIGS. 7 to 9). T-shaped wing elements 8 are mounted to the outer annular sidewall 10 of the hub on each side of the open end 12 and comprise a stem part 8A and curved distal end 8B. The wing elements are adjustable from an open tensioned configuration illustrated in FIGS. 1 to 5 where the wings are configured to nest in corresponding recesses 15 formed on an outer surface of the distal end 3 of the catheter, and a closed configuration illustrated in FIG. 8 where the wings project across the open end 12 of the hub. The wing elements are generally formed from a shape memory material and are biased into the closed configuration.

Figure 2:
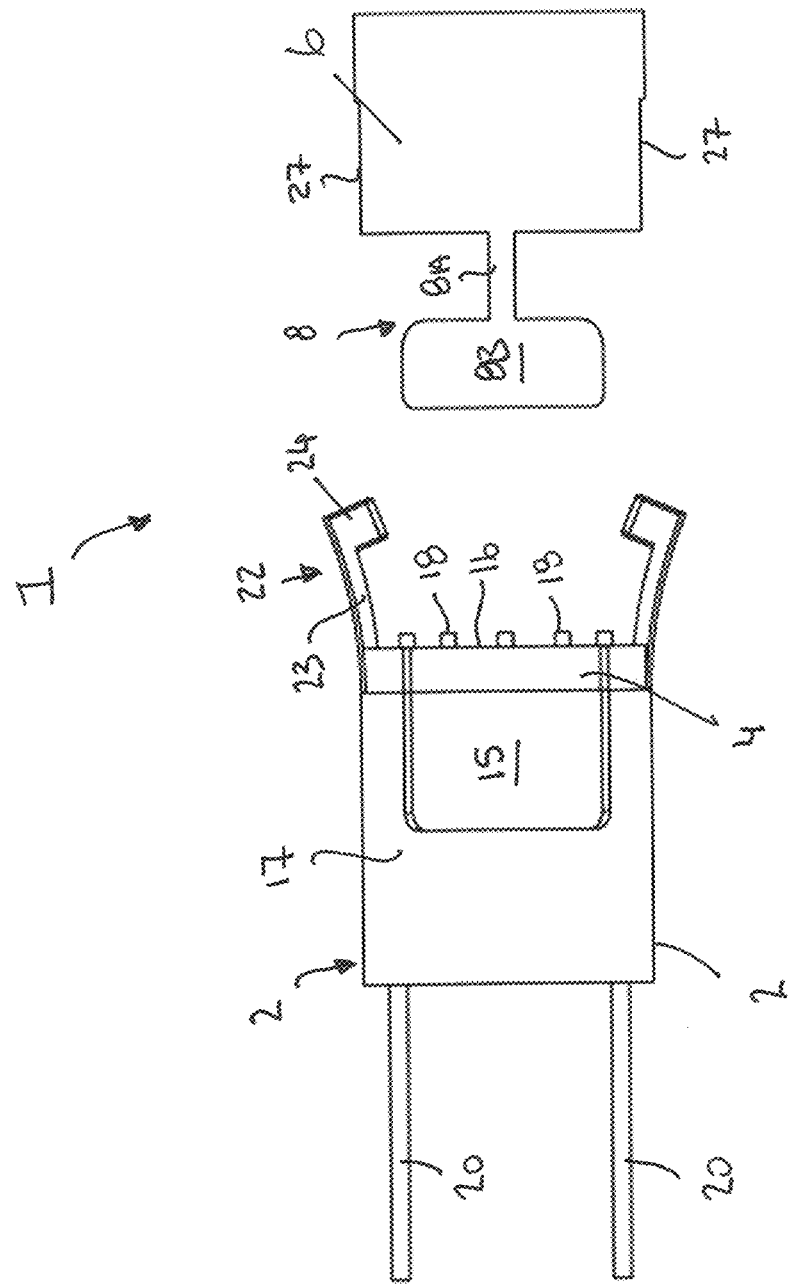
FIG. 2 is a side elevational view of the catheter and proximal connecting hub of FIG. 2 (decoupled configuration).
Figure 3:
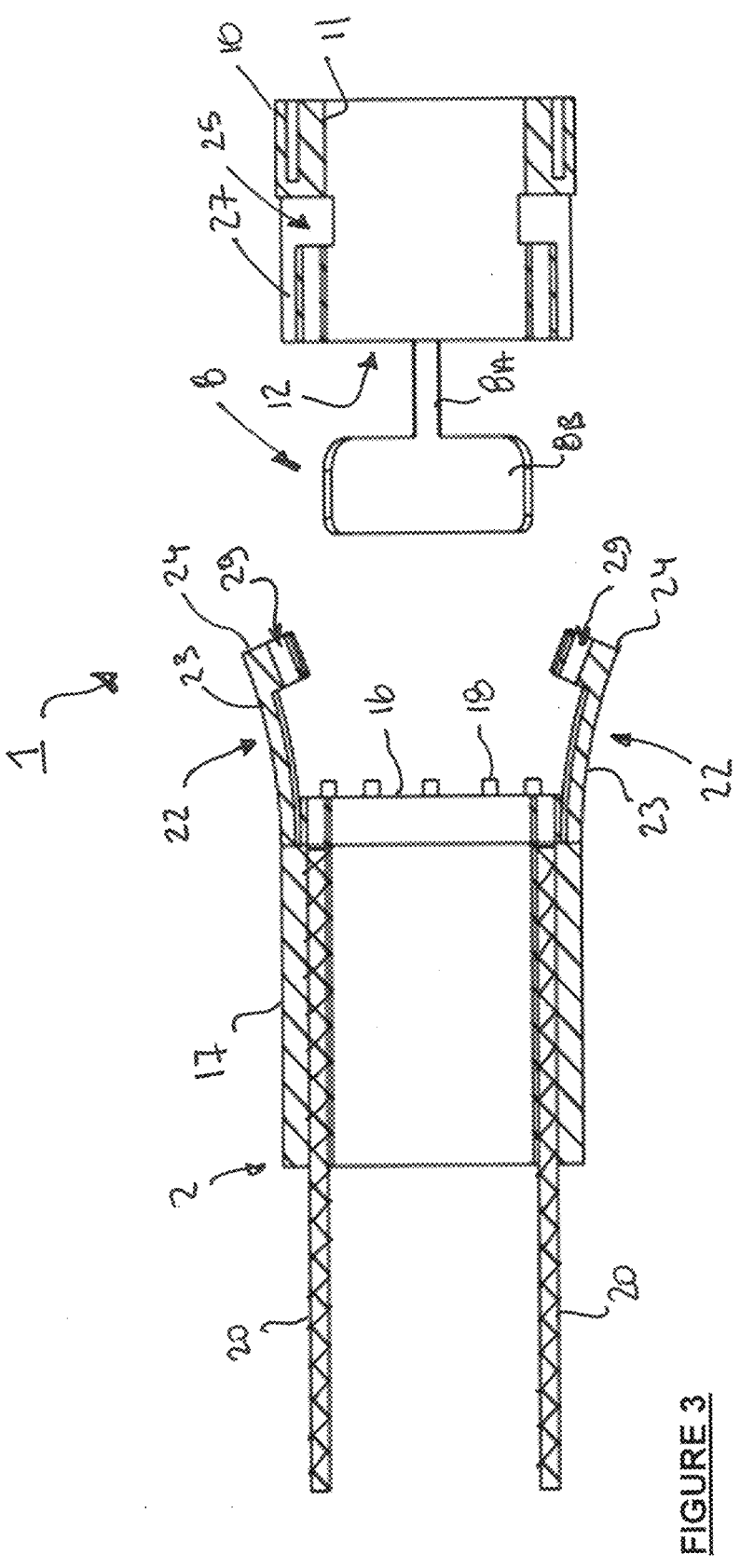
FIG. 3 is a sectional view of the catheter and proximal connecting hub of FIG. 2 (decoupled configuration) showing the locking bolt in a retracted configuration.

Referring to FIGS. 1 to 3 the distal end of the catheter comprises an annular housing 17 coupled to the first electrical connector 4 provided by an annular end plate having ten electrical connection pins 18 that extend axially proud of a distal end of the plate, including five pins disposed on one side of the plate and five pins disposed on an opposite side of the plate. Each electrical connection pin is electrically coupled to a conducting wire (not shown) that extends through the catheter to a proximal end of the plate where is it coupled to an electrical supply through a handle. The catheter also includes elongated locking rods 20 disposed on each side of the catheter and an actuation system to move the move the rods axially with respect to the catheter. The actuation system is disposed in a handle of the catheter is configured such that the rods are generally biased into an extended position and actuatable to retract the rods when desired. The annular end plate has apertures that allow the locking rods 20 pass axially through the plate. The distal face 16 of the first electrical connector is dimensioned to abut a proximal end of the inner sidewall 11 of the hub 6 when the catheter and hub are coupled together, with the electrical connection pins 18 projecting into the corresponding electrical sockets to electrically couple the first and second electrical connectors.

The annular housing 17 of the catheter comprises arms 22 disposed on each side of the housing that extend distally away from the catheter and curve radially outwardly as shown in FIGS. 1 to 3. Each arm has a leg part 23 and a grab part 24 oriented inwardly of the leg part having a socket 29 and is formed from a resiliently deformable material to allow the legs to be resiliently deformed from a relaxed outwardly curved shape shown in FIGS. 1 to 3 (unlatched configuration) to a tensioned straight configuration shown in FIGS. 4 and 5 (latched configuration). Thus, the arms function as a latch to mechanically couple the catheter and hub together. The outer annular sidewall 10 and inner annular sidewall 11 of the hub have apertures 25 disposed on each side of the hub configured to receive the grab parts 24 of the arms when the arms are deformed into the straight tensioned configuration. The locking rods 20 of the catheter are configured to be extended into engagement with the socket 29 of the grab part 24 to lock the grab part and arms in a latched configuration.

An outer surface of the outer annular sidewall 10 comprises recesses 27 dimensioned to receive the leg part 23 of each arm 22 when the leg is deformed into the tensioned straight configuration shown in FIG. 4B.

Referring to FIGS. 7 to 9, the implantable occlusion apparatus 5 (implant) is shown in more detail, in which parts described with reference to the previous figures are assigned the same reference numerals. The implantable occlusion apparatus 5 comprises a cylindrical mesh cage 30 with a recessed (concave) proximal end 31 and an open distal end 32. The proximal connection hub 6 is provided on the proximal end, distal of a blood-impermeable cover membrane 33 having a slitted aperture 34. An array of eight electrodes 35 are provided circumferentially around the wall of the occlusion apparatus at equally spaced apart locations. Each electrode 35 is connected to the connecting hub 6 with dedicated electrical leads 14. Referring to FIG. 8, the proximal connecting hub 6 is illustrated with the blood-impermeable cover membrane 33 removed for clarity. The T-shaped wing elements 8 are shown in an un-tensioned configuration folded over the open proximal end 23 of the connecting hub 6 and FIG. 9 shows the wing elements inf the same configuration and with the cover shown covering the open end of the hub to prevent ingress of blood through the hub of the implant. FIG. 5 is the same as FIG. 4 but with the blood impermeable cover membrane 13 shown covering the open proximal end 23 of the hub 6.

In use, the system is assembled by opening the wings of the occlusion apparatus and bringing the distal end of the catheter and proximal end of the hub together in register until the electrical pins of the catheter engage the sockets of the hubs. The latching arms are then deformed into the straight tensioned configuration until the grab parts project into the apertures on each side of the hub. While in this position, the actuation system of the locking rods is actuated to advance the rods distally through the catheter and into the projecting hub where they engage the socket of the respective grab parts, locking the grab parts and arms in engagement with the hub. The system is then assembled with the first electrical connector and second electrical connector electrically coupled and the catheter mechanically locked to the hub.

The system is then advanced percutaneously to a target location in a body lumen (in the case exemplified above, the LAA) and the position of the implant is then checked using a contrast dye and x-ray imaging. Once the position is correct, the electrodes of the implant are actuated to perform a tissue ablation or tissue sensing procedure. Tissue ablation may be performed first, using non-thermal pulsed field ablation, and then the electrodes may be employed in a sensing mode to determine an electrical parameter of the tissue such as electrical impedance which can be correlated with electrical isolation of the tissue.

Once the treatment or diagnosis is completed, the catheter is detached from the implant by retracting the locking rods out of engagement with the grab parts, whereby the arms disengage with the hub and return their un-tensioned outwardly curved configuration. Once unlatched, the catheter can be retracted to electrically de-couple the first and second electrical connectors and the catheter is then withdrawn transluminally leaving the implant in-situ in the body lumen. The catheter may be re-attached to the implant at a later date and radially retracted and withdrawn transluminally.

Figure 6A:
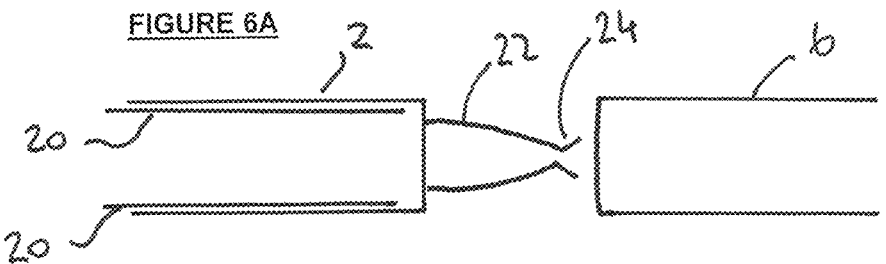
FIG. 6A is an illustration of an alternative catheter having latching arms that extend radially inwardly and are that are resiliently deformable into a substantially straight configuration to engage an inside of the sidewall of the proximal hub.
Figure 6B:
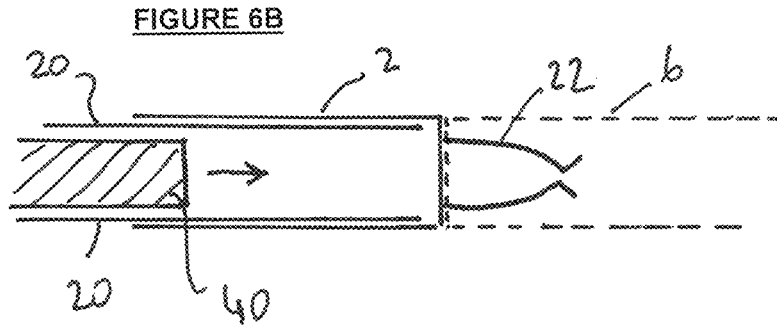
FIG. 6B is another illustration of the alternative catheter of FIG. 6A with an expander element in an unadvanced position.
Figure 6C:
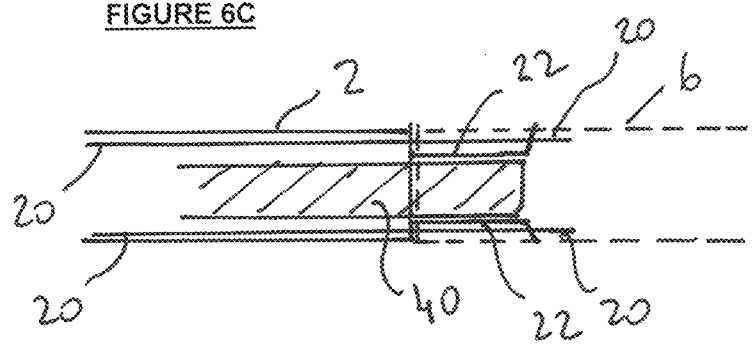
FIG. 6C is another illustration of the alternative catheter of FIG. 6A with the expander element in an advanced position and the latching arms extended into a substantially straight configuration.

FIGS. 6A to 6C illustrates another embodiment of the invention in which parts described with reference to the previous embodiments are assigned the same reference numerals. In this embodiment the arms 22 extend distally and radially inwardly in a curved configuration (FIGS. 6A and 6B) and are resiliently deformable into an axial straight configuration (FIG. 6C) where the grab parts of the arm 24 engage an aperture on the inside of the sidewall of the hub. Locking bolts 20 as described previously are provided to engage a socket on the grab parts of the arms. As illustrated in FIG. 6A, the arms curved inwardly and are configured to extend into the lumen of the hub 6 when the hub 6 and catheter are coupled together as shown in FIG. 6B. An expander element 40 can be advanced through the lumen of the catheter and into the hub 6 to force the arms radially outwardly as shown in FIG. 6C where the grab parts of the arms engage an aperture (not shown) on the sidewall of the hub, and the locking bolt can be extended into the hub to engage the grab parts and lock the arm in the latched position. After use in-vivo, the locking bolts can be retracted and release the latching arms which spring back into the relaxed radially inward configuration, thereby releasing the catheter from the hub.

The system of the invention may be employed to deliver a detachable implant to a target location in the body, supply electrical energy to the implant which it is still attached to the catheter, and then be released and electrically decoupled from the catheter. The system allows use of a catheter and implant that are configured for connection by rotation of one relative to the other (for example threaded engagement or a twist-lock connection mechanism) while allowing the user of electrical connectors that employ electrical pins and sockets configured for coupling and decoupling by axial movement of one relative to the other. The embodiments described above are for occlusion and electrical isolation of the LAA by tissue ablation electrodes forming part of the occlusion apparatus. However, the system is applicable for use with other types of implants.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A system comprising:
an elongated catheter comprising a proximal end configured for operative coupling to an electrical power source, a distal end with a first electrical connector and a first conducting wire to electrically couple the electrical power source with the first electrical connector;
an implant comprising a tissue energising module and a proximal connecting hub configured to detachably couple with the distal end of the elongated catheter by axial movement of the elongated catheter relative to the proximal connecting hub, the proximal connecting hub comprising a second electrical connector configured to mate with the first electrical connector and electrically coupled the first electrical connector with the tissue energising module through a second conducting wire; and
a latch system to lock the distal end of the catheter to the proximal connecting hub comprising:

an arm attached to the distal end of the catheter that is resiliently deformable from a radially outward or radially inward unlatched configuration to a tensioned latched configuration in which the arm engages a sidewall of the proximal connecting hub; and
a locking element that is axially adjustable from a retracted orientation to a distally extended orientation in which the locking element retains the arm in the latched configuration.

2. A system according to claim 1, in which the locking element comprises a locking bolt disposed in the distal end of the catheter that is axially adjustable from a retracted orientation to a distally extended orientation in which the bolt engages the arm in the latched configuration.

3. A system according to claim 2, in which the proximal connecting hub comprising the sidewall including an aperture, and the arm comprises a grab part with a socket configured to protrude through the aperture when the arm is in the tensioned radially inward or radially outward latched configuration, wherein the locking bolt is configured to engage the socket when in the distally extended orientation.

4. A system according to claim 1, including a first latch disposed on one side of the distal end of the catheter and a second latch disposed on an opposite side of the distal end of the catheter.

5. A system according to claim 1, in which the arm is curved radially outwardly and resiliently deformable to a tensioned straight configuration.

6. A system according to claim 1, in which the sidewall of the proximal connecting hub comprises a recess to receive the arm whereby when the arm is in the tensioned radially inward latched configuration, an external surface of the arm is flush with an external surface of the sidewall.

7. A system according to claim 1, in which the distal end of the catheter comprises a distal face and the proximal end of the proximal connecting hub comprises a proximal face, wherein distal and proximal faces abut when the catheter and proximal connecting hub are coupled together, and wherein the distal face comprises electrical pins and the proximal face comprises corresponding electrical sockets configured to receive the electrical pins.

8. A system according to claim 7, in which the first electrical connector comprises a first section disposed on one side of the distal face and a second section disposed on an opposite side of the distal face and the second electrical connector comprises a first section disposed on one side of the distal face and a second section disposed on an opposite side of the distal face.

9. A system according to claim 1, in which the tissue energising module comprises a tissue ablation electrode.

10. A system according to claim 1, in which the implant is a radially expansible occlusion apparatus for occluding a body lumen and is adjustable between a contracted orientation suitable for transluminal delivery and a deployed orientation configured to occlude the body lumen.

11. A system according to claim 10, in which the implant is a radially expansible occlusion apparatus for occluding a left atrial appendage of the heart.

12. A system according to claim 1, in which the proximal connecting hub of the implant comprises an annular sidewall that defines an open proximal end and two wing elements mounted to the sidewall on opposed sides of the open proximal end that are configured for movement from an at rest closed configuration in which the wing elements are folded over the open proximal end of the raised connecting hub to an open tensioned configuration.

13. A system according to claim 12, in which a radially outer wall of the distal end of the catheter comprises surface recesses configured to receive the wing elements of the proximal connecting hub in a nested flush configuration when the distal end of the catheter and proximal connecting hub are connected together.

14. A system according to claim 1, in which one of the first electrical connector and second electrical connector comprises a housing with one or more electrical sockets and another of the first electrical connector and second electrical connector comprises a housing with one or more electrical pins corresponding to the one or more electrical sockets.

15. A system according to claim 14, in which the housing of the electrical connector comprising the or each electrical pin comprises a resiliently deformable sidewall in which the or each electrical pin projects proud of the resiliently deformable sidewall.

\* \* \* \* \*